United States Patent [19]

Smith et al.

[11] Patent Number: 5,475,728
[45] Date of Patent: Dec. 12, 1995

[54] EUCENTRIC MOTION SYSTEM

[75] Inventors: James A. Smith, Waterloo; Miroslav J. Stehlik, Kitchener; Matthew R. Atkinson, Waterloo; John H. Cole, Kitchener; Arthur E. Dixon, Waterloo; James H. Fierling; John Hennessy, both of Kitchener; Christopher J. L. Moore, St. Jacobs, all of Canada

[73] Assignee: Waterloo Scientific Inc., Waterloo, Canada

[21] Appl. No.: 100,274

[22] Filed: Aug. 2, 1993

[30] Foreign Application Priority Data

Aug. 3, 1992 [GB] United Kingdom .................. 9216461

[51] Int. Cl.$^6$ .................................................. G01N 23/20
[52] U.S. Cl. ............................................ 378/81; 378/208
[58] Field of Search ................................ 378/79, 80, 81, 378/208

[56] References Cited

U.S. PATENT DOCUMENTS 5,197,089  3/1993  Baker ........................................ 378/34

Primary Examiner—Craig E. Church
Attorney, Agent, or Firm—Daryl W. Schnurr

[57] ABSTRACT

A motion system or goniometer for moving a sample supported by the system has a triangular plate supported at each apex by actuators that can extend or retract axially independently from one another. The actuators are mounted on x-y translation stages and a θ rotation stage. The movement of the actuators, translation stages and rotation stage is controlled by a computer. When it is desired to create a rocking curve at a particular position on the sample, the translation stages and rotation stage can remain stationary while moving only the plate and actuators. The goniometer is much more efficient and less expensive than previous devices which require movement of the entire goniometer when creating a rocking curve.

18 Claims, 10 Drawing Sheets

EUCENTRIC MOTION SYSTEM

BACKGROUND OF THE INVENTION

1. Field of the Invention

This invention relates to motion systems, including goniometers, for rotating, translating, tilting and/or rocking a sample, for example, in a Double Crystal X-ray Diffractometer (henceforth DCD). More particularly, this invention relates to a goniometer used in a mapping DCD, where rocking curves are measured at a large number of locations on semi-conductor wafers or in other instruments requiring a eucentric mapping goniometer.

2. Description of the Prior Art

It is known to have mapping DCD's that use x-y stages added to a sample motion system that performs sample tilt alignment and rocks the sample so that a rocking curve may be recorded at a large number of positions on the sample to produce an X-ray map of the sample. Since the axis about which the rocking motion occurs is on the plane of the sample and must pass through the particular sample position upon which an X-ray beam coming from a first crystal impinges, previous DCD's rock the sample, sample holder and the x-y stages about that axis. After a rocking curve is recorded at one sample position, the x-y stages move the sample so that a new measurement point on the sample is positioned relative to the X-ray beam and a new rocking curve is recorded at that position. This procedure is continued until an X-ray map of the sample has been obtained. Since the x and y stages as well as the sample and sample holder are rocked each time a rocking curve is measured, previous motion systems or goniometers are relatively slow and can be relatively expensive. For example, when a sample is such that thousands of measurements are required to map it at high spatial resolution, several hours or even days may be required to map the entire sample (see the paper by Halliwell, et al. entitled "Assessment of Epitaxial Layers by Automated Scanning Double Axis Diffractometry", published in the Journal of Crystal Growth 65 (1983), pages 672–678 and the paper by Macrander, et al. Entitled "X-ray, Photoluminescence, Stoichiometry, and Thickness Mapping of $In_{1-x}Ga_xAs_yP_{1-y}$", published in the Journal Electrochemical Society, Vol. 138, No. 4, in April, 1991, at pages 1147–1153.

SUMMARY OF THE INVENTION

It is an object of the present invention to provide a motion system or goniometer whereby a rocking curve can be created for a particular position of the sample by moving only a plate and supporting actuators.

An X-ray apparatus comprising an X-ray source for generating an X-ray diffraction beam and a motion system is provided for moving a sample supported by said system. The system has a surface for supporting said sample x-y translation stages and a rotation stage, said stages being located beneath said surface. The surface is pivotally supported by three legs that are spaced apart from one another, with means for moving said legs relative to one another, thereby moving said surface, said means for moving being mounted on one of the said x-y translation.

A method of using a motion system as a goniometer is provided where said motion system has a plate that is mounted on three actuators that are spaced apart from one another and are independently axially extendable and retractable. The actuators are supported by x-y translation stages and by a rotation stage. The actuators, translation stages and rotation stage are controlled by a computer. The method comprises placing a sample supported by a holder onto said plate, activating the rotation stage, translation stages and actuators to correctly position said sample relative to an X-ray beam from a diffractometer, rocking and tilting said sample by moving only the plate and actuators while taking appropriate measurements to establish a rocking curve for that position, moving the translation stages and rotation stage as required to a second position and rocking and tilting the sample by moving only the plate and actuators while taking appropriate measurements to establish a rocking curve for said second position, repeating this procedure for other positions on said sample.

DESCRIPTION OF A PREFERRED EMBODIMENT

Figure 1A:
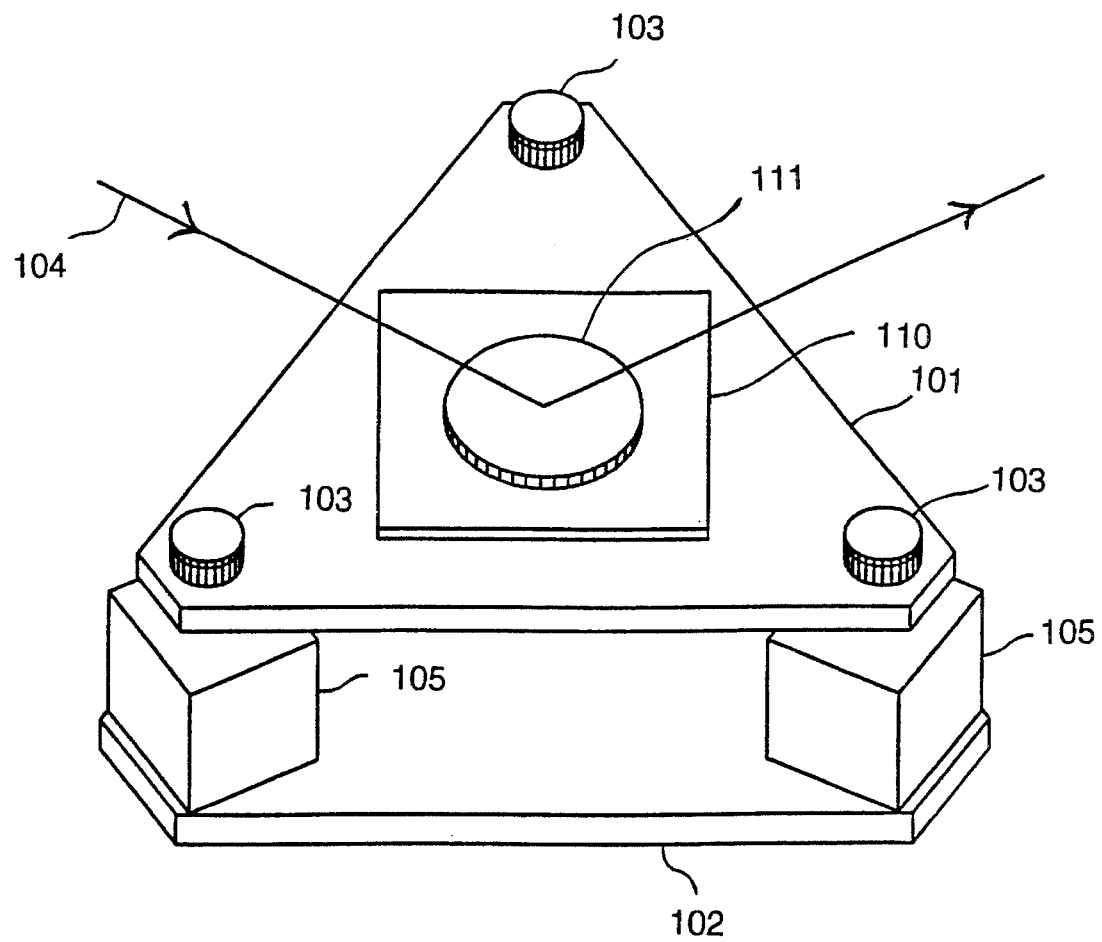
FIG. 1(a) is a perspective view of a goniometer having a triangular plate mounted on three actuators.

In FIG. 1(a), there is shown a goniometer in which a triangular plate or surface 101 is mounted on three linear actuators 105, three support bearings 103 and a first base plate 102. The plate 101 supports a sample 111 in a sample holder 110. The bearings provide for universal movement between the surface and the actuators.

Figure 1B:
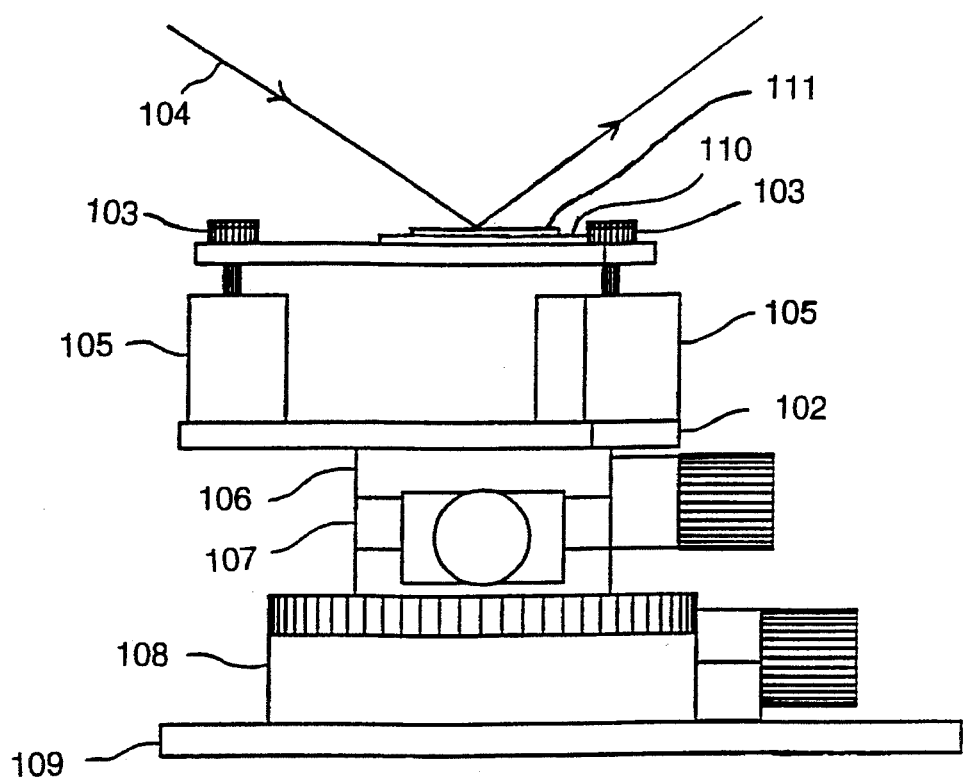
FIG. 1(b) is a side view of the goniometer of FIG. 1(a) mounted on an x-y stage and a rotation stage.

As shown in FIG. 1(b), the goniometer of FIG. 1(a) is mounted on x-y translation stages 106, 107 respectively, which in turn, are mounted on a rotation stage 108. The rotation stage 108 is in turn mounted on a second base plate 109.

Figure 1C:
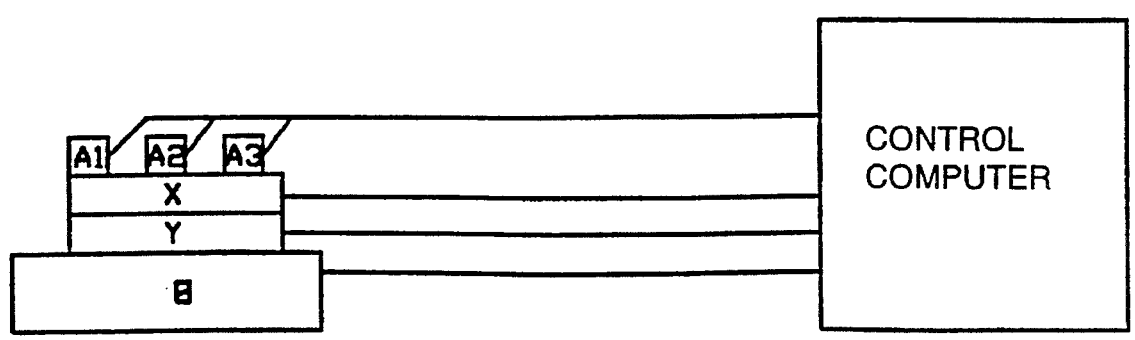
FIG. 1(c) is a block circuit diagram showing the goniometer of FIG. 1(b) connected to a control computer.

The actuators 105 are pivotally mounted to the plate 101 by bearings 103. Each corner of the triangular plate can be moved in a vertical direction by activating the linear actuators which can be axially extended or retracted independently of one another. Thus, an angular orientation of the sample can be varied as well as a vertical height of the sample above the base plate. The degree of extensions or retractions of the three linear actuators required for rock, tilt and height variations are calculated and controlled by a computer connected as shown in FIG. 1(c). The computer also controls the x-y translation stages 106, 107 and the rotation stage 108.

In FIG. 1(a), there is shown an X-ray beam 104 coming from a first crystal (not shown) of a DCD (not shown). The first crystal of the DCD and the DCD are conventional and are therefore not further described. The beam 104 impinges on the sample 111 at a specific point. Since the beam 104 is fixed in space, a height of the point of impingement on the sample, measured above the base plate, must be kept constant during any motion about the rock and tilt axes, as well as any motion in the x and y directions. Since the point of impingement of the beam 104 on the sample 111 is on the θ axis of the goniometer, directly above the center of the rotational stage 108, no height change is necessary when the θ stage rotates. Computer control of the three linear actuators, the x and y stages and the rotation stage allows the sample to be rotated in θ to achieve a proper sample alignment with the incoming beam, then tilted to optimize sample tilt alignment, and finally rock to record a rocking curve. The sample is then moved to a new position using the x-y stages and the height above the base plate is adjusted, if necessary, by changing the extension of the three linear actuators. The sample is then rocked to record a second rocking curve for this second position. This procedure is repeated for other positions until the sample has been mapped by measuring rocking curves on a rectangular (or other shape) grid of positions across the entire sample.

A simpler version of the goniometer shown in FIG. 1(b) can be used in a single-point DCD. Since no mapping capability is required in this simple version, the x and y stages can be removed and the assembly of FIG. 1(a) can be mounted directly on the rotating stage. If the sample is rotated manually for initial alignment, then the rotating stage is not required and the goniometer shown in FIG. 1(a) containing only linear actuators, when combined with a control computer, will still provide the basic tilt and rock motions necessary for a DCD.

Figure 2A:
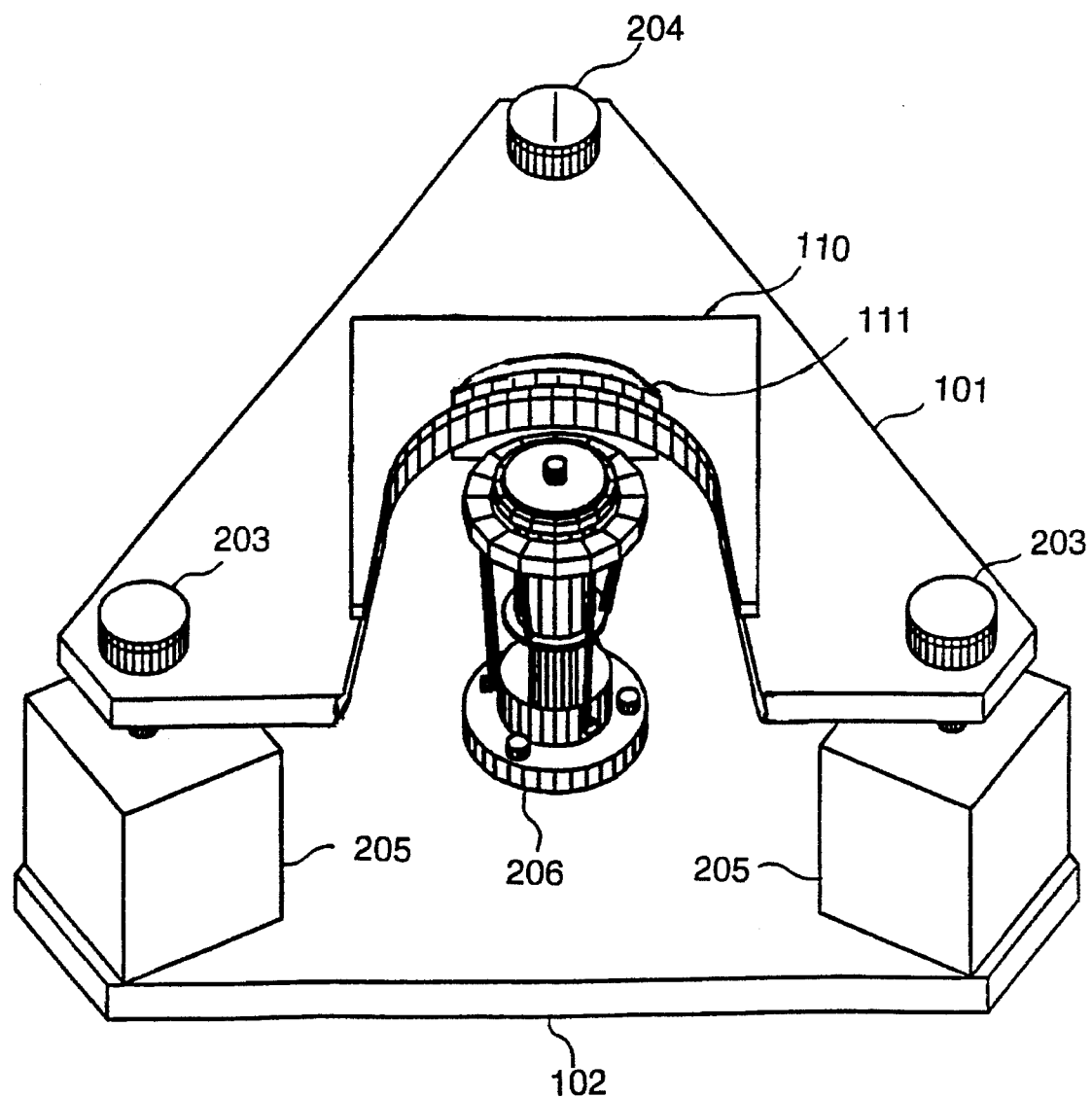
FIG. 2(a) is a perspective view of a further embodiment of a goniometer showing a cut-away portion exposing a centrally located stabilizer assembly.

In FIG. 2(a), there is shown a further embodiment of a goniometer where the triangular plate 101 is supported by two flat support bearings 203 and one grooved prismatic support bearing 204. A stabilizer assembly 206 provides precise controlled movement and ensures that a center of a surface of sample 111 mounted on the triangular plate 101 remains substantially equidistant from the three linear actuators 205 during rock and tilt motions. The grooved prismatic support bearing 204 ensures that the triangular plate 101 does not rotate about the vertical (θ) axis during rock and tilt motions.

Figures 2B, 2C:
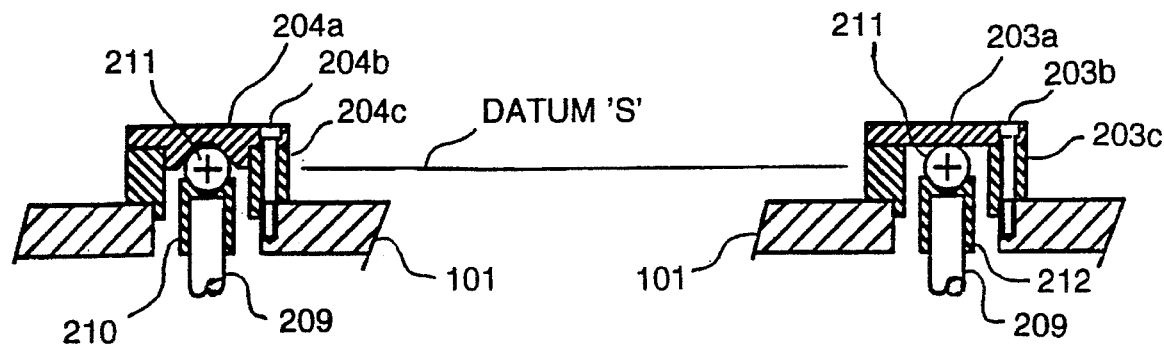
FIG. 2(b) is a sectional side view of a prismatic support bearing.
FIG. 2(c) is a sectional side view of a flat support bearing.

In FIG. 2(b), there is shown a detailed view of the grooved prismatic support bearing 204. Lifter 209 from one of the linear actuators 205 exerts a force on ball support 210 and ball 211. The ball 211 in turn exerts a force on the grooved prismatic support bearing 204a. The bearing 204a is attached to bearing extension 204c and to triangular plate 101 by fastener 204b. The axis of the prismatic support bearing is oriented towards a center of triangular plate 101.

FIG. 2(c) shows a detailed view of the two flat support bearings 203. It can be seen that lifter 209 supports a ball support 212, which in turn supports ball 211 as shown. The ball 211 pushes on flat support bearing 203a. Bearing extensions 203c and 204c have the appropriate length to place the center of balls 211 for all of the bearings in the same plane as a plane through the sample 111. The plate is held on the balls by gravity.

Figure 2D:
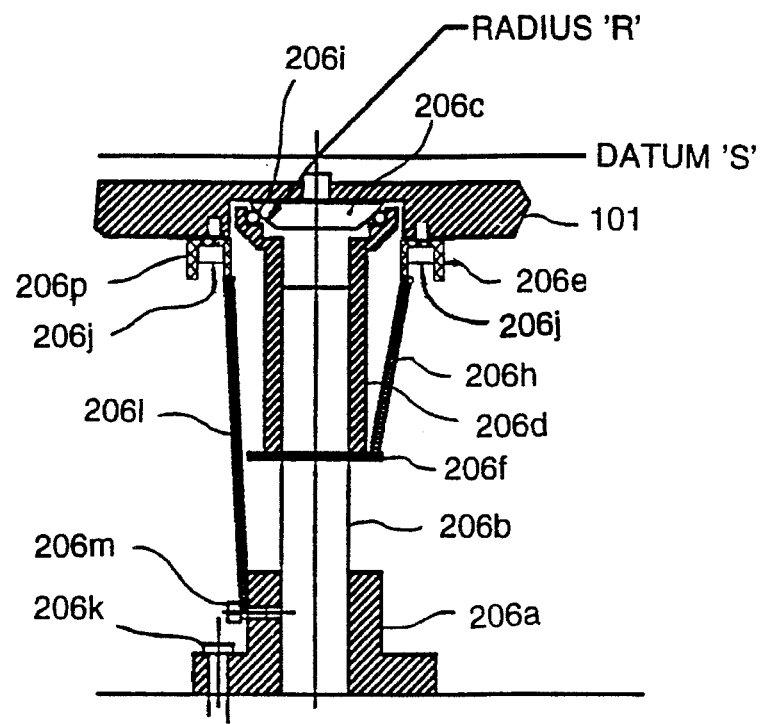
FIG. 2(d) is a sectional side view of said stabilizer assembly.

In FIG. 2(d), there is shown a sectional side view of the stabilizer assembly 206. Base flange 206a supports post 206b. Cylindrical slider 206d slides along post 206b. Balls 206i support spherical bearing 206c, whose radius (R) equals a distance from a point of contact of balls 206i on a bearing surface of spherical bearing 206c to a point on the sample at which the rock and tilt axes converge. Tension spring 206h is attached to triangular plate 101 by spring retainer 206e, which is attached to triangular plate 101 by fastener 206j. An opposite end of the spring 206h is attached to spring support ring 206f, which is located beneath slider 206d, thus holding the spherical bearing 206c firmly in contact with the balls 206i. Second spring 206l is attached to triangular plate 101 by spring retainer 206p and fastener 206j. Second spring 206l is attached to base flange 206a with fastener 206m. The second spring 206l ensures that plate 101 does not lose contact with the three linear actuators during rapid motion of said actuators.

Figure 3:
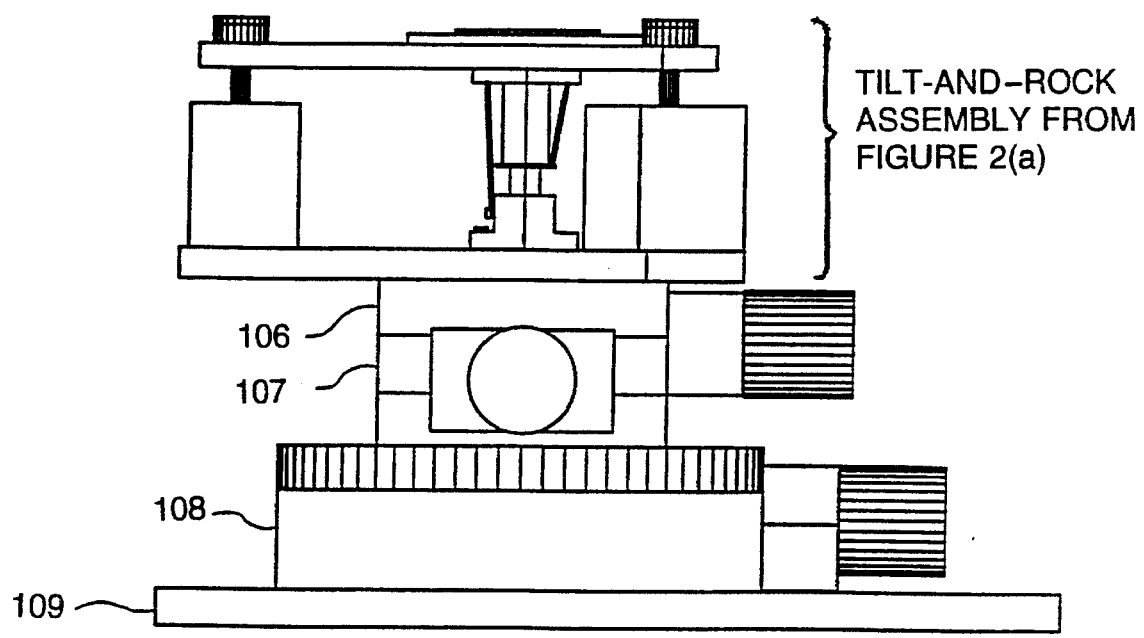
FIG. 3 is a side view of the goniometer of FIG. 2(a) mounted on an x-y stage and a rotation stage.
Figure 4:
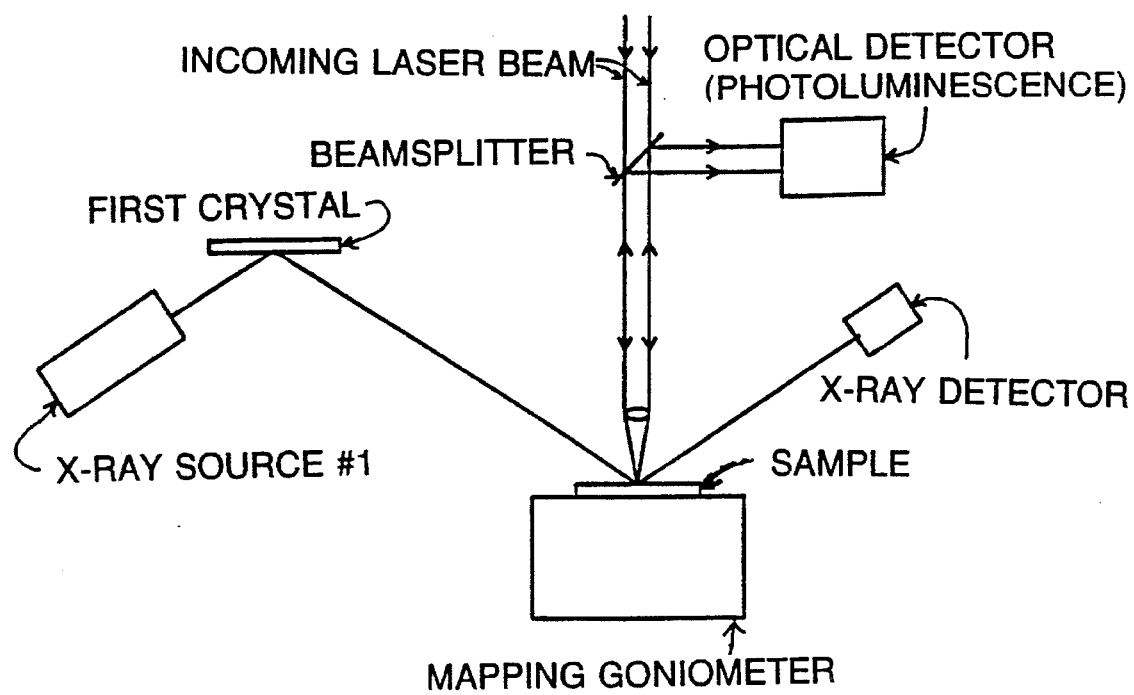
FIG. 4 is a block diagram of a mapping DCD using a eucentric goniometer.

FIG. 3 shows the embodiment of FIG. 2(a) mounted on x-y translation stages 106, 107 and rotation stage 108, which in turn is mounted on base plate 109. In FIG. 4, a goniometer of the present invention is used with a mapping DCD in combination with a scanning photoluminescence mapping system allowing simultaneous or sequential measurement of DCD rocking curves and photoluminescence spectra from the same sample position. This combination is especially useful for characterizing wafers and epitaxial layers of quaternary semi-conductor compounds.

Figure 5:
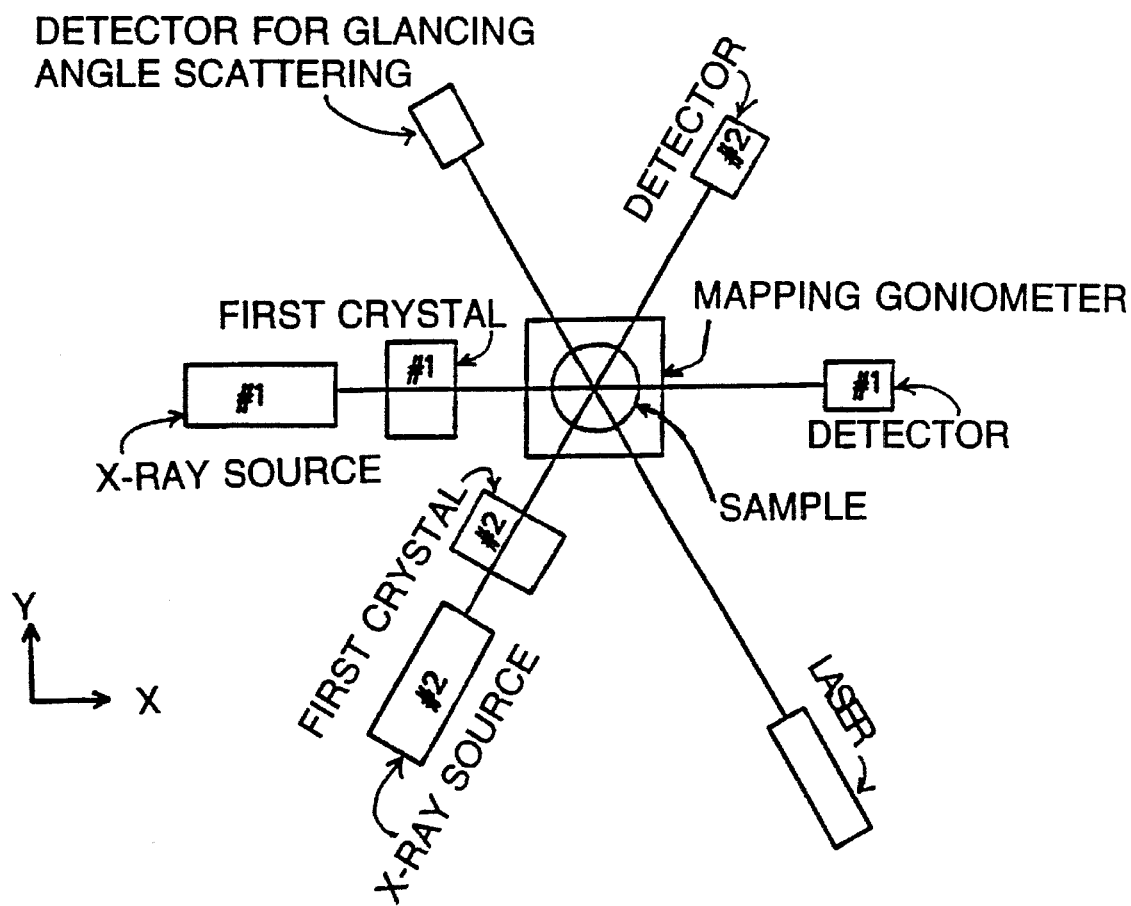
FIG. 5 is a block diagram of a two wavelength, two-axis mapping DCD using a eucentric goniometer.

In FIG. 5, there are shown several other possible combinations with which a goniometer in accordance with the present invention can be used. For example, in one combination, a two-wavelength DCD, in which two DCD arms, each comprising an X-ray source, first crystal and detectors are pre-aligned to perform measurements at the same point in the sample. Either a single point measurement or a complete wafer map can be performed with one DCD arm. Then, the sample can be rotated so that a second measurement or map can be performed with the second DCD arm at a different wavelength. This allows the operator to quickly change from one wavelength to another, without having to change and/or align the X-ray source, first crystal and detector each time a wavelength change is made. In addition, several other uses of the new mapping goniometer are possible either in combination with the DCD, or separately. Another example shown in FIG. 5 is a glancing-angle laser scattering system in combination with the two-wavelength DCD.

Figure 6A:
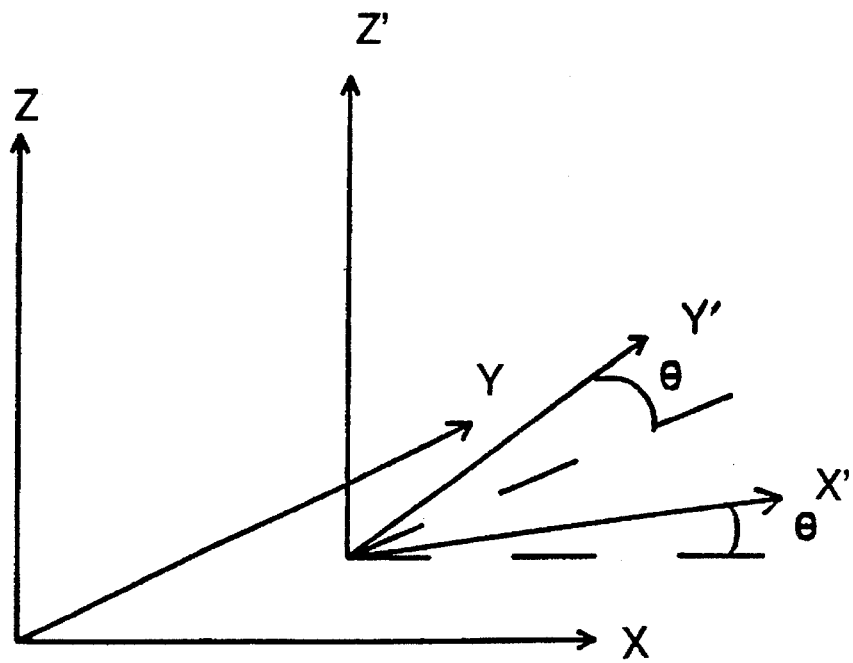
FIG. 6(a) shows a primed (translated and rotated) co-ordinate system and an unprimed (laboratory) co-ordinate system.
Figure 6B:
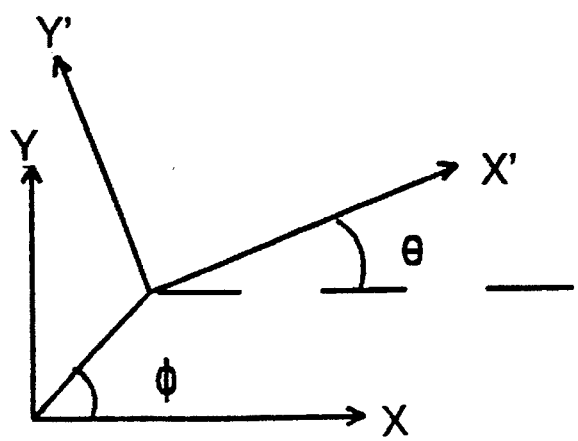
FIG. 6(b) shows co-ordinates of FIG. 6(a) from the z axis.
Figure 6C:
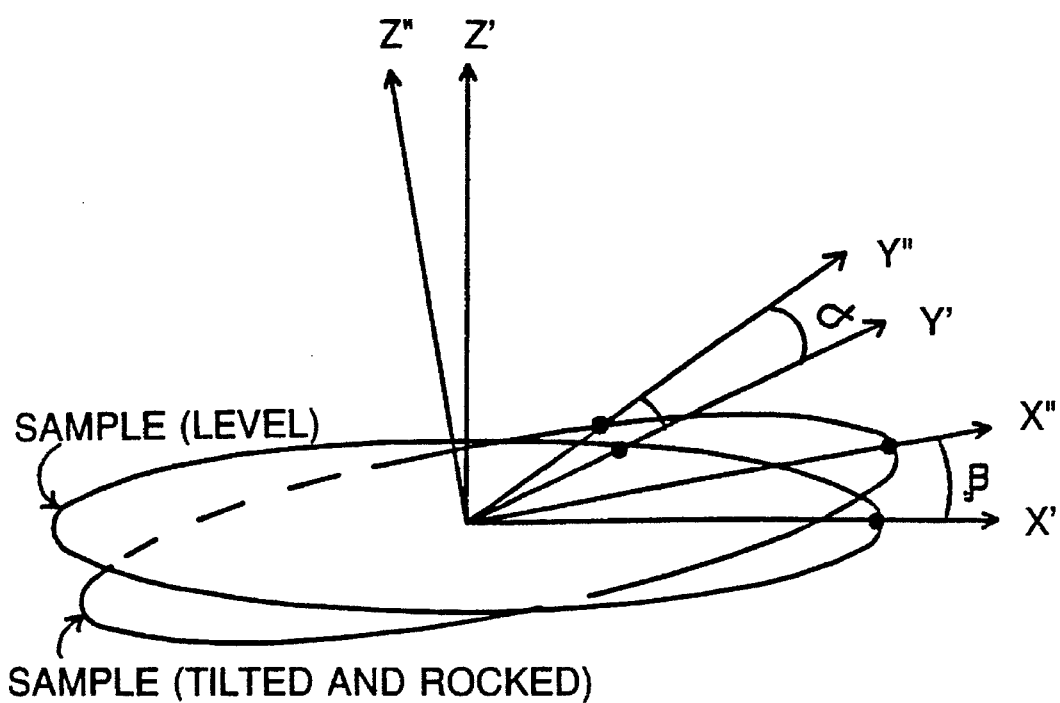
FIG. 6(c) shows prime co-ordinates for a level sample and double prime co-ordinates for a rocked and tilted sample.

In FIGS. 6(a), 6(b) and 6(c), there are shown co-ordinate systems which are used with the following equations for the embodiment of the invention shown in FIG. 3. The derivation of these equations assumes that the centers of the balls 211 and a center of curvature of spherical bearing 206(c) all lie in the same plane as a top surface of sample 111 and, further assumes that balls 211 are small. These co-ordinate systems are as follows:

1) x, y, z (or θ) is a co-ordinate system attached to the machine itself (the "laboratory" coordinate system). The incoming and outgoing X-ray beams are in the x-z plane, and the incoming beam impinges on the sample at x=y=z=0. Tilting of the sample occurs about the x-axis, rocking about the y-axis. α is the angle of the tilt, β is the angle of rock, measured from the x-y plane.

2) x', y', z' is a co-ordinate system attached to the sample at its center, with z' parallel to z, but this co-ordinate system may be rotated through an angle θ and translated on the x-y translation stages through a distance x', y'. This co-ordinate system is used to set the positions of the rotating table and the x-y translation tables.

3) x", y", z" is a co-ordinate system attached to the sample at its center, and is the same as the primed co-ordinate system except it has also been tilted about x and rocked about y. $A_1$, $A_2$, and $A_3$ are the extension of the three linear actuators from their equilibrium positions.

When $A_1=A_2=A_3=0$, the wafer is level and the incoming beam strikes the wafer at the correct height (measured along the z-axis).

A summary of the equations required to translate, rock and tilt this new mapping goniometer are given below:

$A_1 = d \tan \beta \cos(180+\theta) + d \tan \alpha \sin(180+\theta) - (x'_1 \tan \beta + y'_1 \tan \alpha)$ (1)

$A_2 = d \tan \beta \cos(-60+\theta) + d \tan \alpha \sin(-60+\theta) - (x'_1 \tan \beta + y'_1 \tan \alpha)$ (2)

$A_3 = d \tan \beta \cos(60+\theta) + d \tan \alpha \sin(60+\theta) - (x'_1 \tan \beta + y'_1 \tan \alpha)$ (3)

where $x'_1 = x''_1 + \Delta x \cos \theta + \Delta y \sin \theta$ (4)

$y'_1 = y''_1 - \Delta x \sin \theta + \Delta y \cos \theta$ (5)

where $\Delta x = x_0(\cos \beta - 1) = r_0 \cos(\phi+\theta)(\cos \beta - 1)$ (6)

$\Delta y = y_0(\cos \alpha - 1) = r_0 \sin(\phi+\theta)(\cos \beta - 1)$ (7)

where $\phi = \tan^{-1}(y''/x'')$ (8)

$r_0 = \sqrt{(x'')^2 + (y'')^2}$ (9)

To move to a sample position $x_1"$, $y_1"$ with initial values of α and β, the x-y stages are moved through a distance $-x_1'$ and $-y_1'$ as shown above. The extensions $A_1$, $A_2$ and $A_3$ for that sample orientation are calculated using equations 1, 2 and 3.

Figure 7:
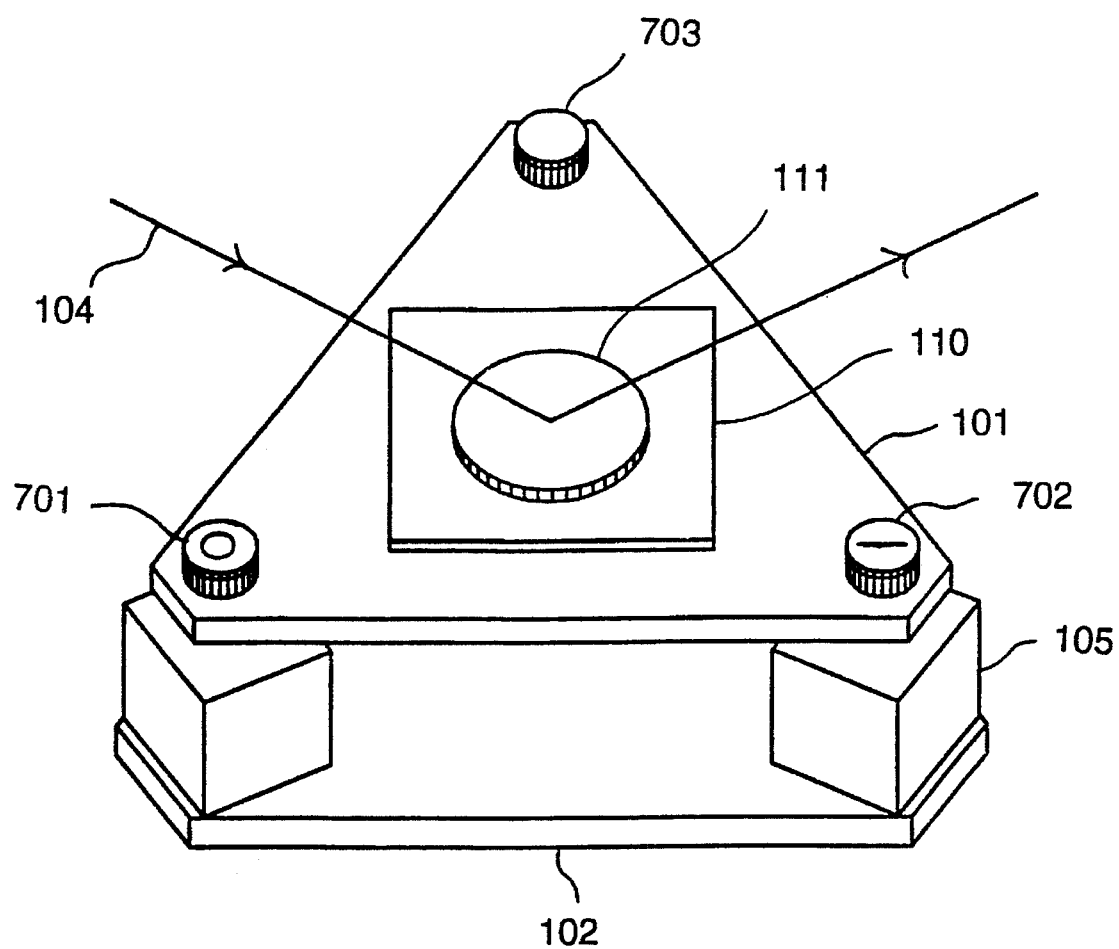
FIG. 7 is a perspective view of a further embodiment of a goniometer using a ball and socket bearing.

The embodiment of the goniometer shown in FIG. 7 is simpler mechanically than the goniometer shown in FIG. 2, but the motion is more complex. In this embodiment, no stabilizer assembly 206 is used so that the sample surface does not constrain to move about its center position. One of three bearings 701 is a ball-and-socket joint, the second bearing 702 is a grooved prismatic bearing with the groove pointing towards the ball-and-socket joint, and the third bearing 703 is a flat plate. Since this orientation for the groove and bearing 702 does not allow the triangular plate 101 to rotate in the θ direction, no θ correction is required during tilt and rock motions but a different set of x' and y' corrections will be required. This embodiment is less expensive to manufacture than the embodiment shown in FIG. 2. The combination of bearings described in this paragraph is not the only combination that can be utilized. For example, if the groove and bearing 702 is oriented toward a centre of the sample, there will be a small θ motion of plate 101 during rock and tilt motions but this can be taken into account by the control computer.

The motion system of the present invention is capable of being able to translate a sample in addition to being able to perform rapid eucentric rotation and rock and tilt motions about each sample position.

Numerous variations can be made within the scope of the attached claims. For example, the stacking order of the stages can be changed (with appropriate changes to the mathematical calculations). For example, the rotation stage can be placed on top of the goniometer assembly shown in either FIGS. 1(a), 2(a) or FIG. 7. Also, the position of the x-y stages and rotation stage can be interchanged but tilt and rock speed may be reduced as the mass that must be tilted and rocked increases. For mapping of certain semi-conductor wafers with a DCD, the wafers are cut with a wafer surface perpendicular to a well defined crystallographic plane. In this situation, either tilt or rotation is required, but not both and the rotation stage can be omitted.

There will also be applications in which only the tilt and rock assembly is required and other applications which use a combination of the tilt and rock assembly with any combination or subset of x stage, y stage and rotation stage.

When the equations where formulated an assumption was made that the balls 211 were small. For finite size balls 211 of radius R, the following correction must be applied to $A_1$, $A_2$, and $A_3$:

$\Delta A_1 = \Delta A_2 = \Delta A_3 = -R(\sec(\tan^{-1}(\sqrt{\tan^2 \alpha + \tan^2 \beta})) - 1)$ (10)

When R is small and α and β are small, this is a very small correction.

The invention has been described as a motion system, which has specifically been defined as including a goniometer. When the invention is used as a motion system, objects could be translated to a particular location or locations and then oriented or moved in a particular manner about that location.

The goniometer motion system can be used to provide a mapping double crystal X-ray diffractometer in which a second X-ray source, second first crystal and second X-ray detector are pre-aligned so that measurements at a second X-ray wavelength can be performed by rotating a sample to the required angle so that the second X-ray map can be performed using the second DCD.

Compared to prior art goniometers, the goniometer of the present invention is relatively inexpensive to construct as it uses commercially available translation, stages, rotation stages and linear actuators. Further, the rock and tilt axes are not mechanically fixed in direction and need not change position when the θ stage rotates as with prior art goniometers. In addition, the most frequent motion in a DCD is the rocking motion and with the goniometer of the present invention, only the mounting plate and sample are rocked. This is a relatively small mass and allows for rapid motion of the sample. In a mapping DCD where thousands of rocking curves are required, this results in a major time saving over prior art DCD's which rock the x and y stages and sometimes the rotation stage as well along with the sample.

The motion system or goniometer of the present invention can be used in any application where it is important to be able to orient a specific point on a surface of or inside a specimen or to map a specimen with respect to a beam of radiation. This new goniometer also allows the specimen to be tilted and rocked about two mutually exclusive perpendicular axes that are in a plane perpendicular to the θ axis, but can be oriented in any direction in that plane. For example, the goniometer may be useful in glancing-angle X-ray reflectometry and diffraction, glancing-angle laser scattering and other applications using beams of X-rays, electrons, neutrons, ions, lights, atoms, etc. where orientation of the specimen with respect to the beam is important and where mapping of the specimen may also be required.

What we claim as our invention is:

1. An X-ray apparatus comprising an X-ray source for generating an X-ray diffraction beam and a motion system for moving a sample supported by said system, said system comprising a surface for supporting said sample, a radiation source producing a beam of radiation, x-y translation stages and a rotation stage, said stages being located beneath said surface, said surface being pivotally supported by three legs that are spaced apart from one another, with means for moving said legs relative to one another thereby moving said surface, said means for moving being mounted on one of said x-y translation stages and said rotation stage, said rotation stage being capable of rotating about a θ axis of rotation, said x-y translation stages being mounted to move said surface in an x-y direction relative to said θ axis, with control means to orient said surface using said means for moving and said stages to maintain a point on said sample at which measurements are taken at an intercept of the X-ray beam with said sample when said sample is contacted by said beam, with eucentric motion occurring about said point by moving only said surface and at least one of said legs.

2. An apparatus and system as claimed in claim 1 wherein one of said legs is fixed and the remaining two legs have means for moving thereat.

3. An apparatus and system as claimed in claim 1 wherein the means for moving is located at two of said legs.

4. An apparatus and system as claimed in claim 1 wherein there are means for moving located at each leg.

5. An apparatus and system as claimed in claim 4 wherein the means for moving is an actuator, each actuator being axially extendable and retractable independently of other actuators.

6. An apparatus and system as claimed in claim 1 wherein the surface is a plate having a triangular shape.

7. An apparatus and system as claimed in claim 1 wherein there is a holder located between said sample and said surface.

8. An apparatus and system as claimed in claim 5 wherein the x-y stages are located between the actuators and the rotation stage.

9. An apparatus and system as claimed in claim 5 wherein the actuators, rotation stage and translation stage are connected so that all movement of the surface is controlled by a computer.

10. An apparatus and system as claimed in claim 5 wherein there is a stabilizer assembly extending between said translation stage and said surface, said stabilizer assembly being centrally located on said surface and being connected to maintain a center point of said surface in a substantially fixed position during rock and tilt motions applied to said surface.

11. An apparatus and system as claimed in claim 10 wherein the actuators are connected to said surface by support bearings that permit the actuators and said surface to pivot relative to one another.

12. An apparatus and system as claimed in any one of claims 5, 8 or 9 wherein one of the three actuators is connected to said surface by a grooved prismatic support bearing that prevents the surface from rotating about an axis parallel to said actuators during rock and tilt motions.

13. An apparatus and system as claimed in claim 11 wherein one of said bearings is a ball and socket joint.

14. An apparatus and system as claimed in claim 11 wherein one of the bearings is a grooved prismatic bearing and another bearing is a ball and socket joint.

15. An apparatus and system as claimed in any one of claims 5, 8 or 9 wherein the three actuators are mounted to said surface in a shape of an equilateral triangle.

16. A method of using a motion system as a goniometer where said motion system has a plate that supports a sample and is pivotally supported by three legs that are spaced apart from one another, with means for moving said legs relative to one another, said means for moving being supported by x-y translation stages and by a rotation stage, said legs, translation stages and rotation stage being controlled by a computer, said method comprising manipulating said means for moving and said stages to properly position a point in said sample where measurements are to take place, and subsequently rocking said sample in a eucentric motion about said point by moving only said plate and said means for moving said plate.

17. A method as claimed in claim 16 including the step of operating said system as a six axis eucentric goniometer.

18. A method of using a motion system as a goniometer where said motion system has a plate that supports a sample and is pivotally mounted on three actuators, that are spaced apart from one another and are independently axially extendable and retractable, said actuators being supported by x-y translation stages and by rotation stage, said actuators, translation stages and rotation stage being controlled by a computer, said method comprising placing a sample supported by a holder onto said plate, activating the rotation stage, translation stages and actuators to correctly position said sample relative to an X-ray beam from a diffractometer, rocking and tilting said sample by moving only the plate and actuators while taking appropriate measurements to establish a rocking curve for that position, moving the translation stages and rotation stage as required to a second position and rocking and tilting the sample by moving only the plate and actuators while taking appropriate measurements to establish a rocking curve for said second position, repeating this procedure for other positions on said sample.

\* \* \* \* \*